(12) United States Patent
Purusothaman

(10) Patent No.: US 11,600,381 B2
(45) Date of Patent: Mar. 7, 2023

(54) SYSTEM FOR REFERRAL MANAGEMENT

(71) Applicant: Payoda Technology Inc., Plano, TX (US)

(72) Inventor: Anand Purusothaman, Jersey, NJ (US)

(73) Assignee: PAYODA TECHNOLOGY INC., Plano, TX (US)

( * ) Notice: Subject to any disclaimer, the term of this patent is extended or adjusted under 35 U.S.C. 154(b) by 356 days.

(21) Appl. No.: 16/862,444

(22) Filed: Apr. 29, 2020

(65) Prior Publication Data

US 2020/0350062 A1    Nov. 5, 2020

Related U.S. Application Data

(60) Provisional application No. 62/841,184, filed on Apr. 30, 2019.

(51) Int. Cl.
*G16H 40/20*     (2018.01)
*G06F 16/2458*   (2019.01)
*G16H 10/60*     (2018.01)
*G16H 80/00*     (2018.01)

(52) U.S. Cl.
CPC ......... *G16H 40/20* (2018.01); *G06F 16/2471* (2019.01); *G16H 10/60* (2018.01); *G16H 80/00* (2018.01)

(58) Field of Classification Search
CPC ........ G16H 40/20; G16H 10/60; G16H 80/00; G06F 16/2471
See application file for complete search history.

(56) References Cited

U.S. PATENT DOCUMENTS

2006/0047537 A1*  3/2006  Brimdyr ................ G16H 15/00
                                                    705/2
2019/0074094 A1*  3/2019  Castellanos ............ G16H 15/00

* cited by examiner

*Primary Examiner* — Pei Yong Weng

(57) ABSTRACT

A system for referral management is provided. The referral management system includes a multi-channel referral consolidator, an inbound referral queue, a communication engine, a workflow engine, an integration engine, a referral analytics module, a report engine, and a management module. The referral management system generates a virtual network between key actors of the referral ecosystem which includes a referral provider, a plurality of patients and a plurality specialist. The referral management system consolidates referrals from multiple sources, facilitates effective communication and exchange between key actors of a referral ecosystem and coordinates end to end referral process till referral closure.

16 Claims, 13 Drawing Sheets

FIG. 8

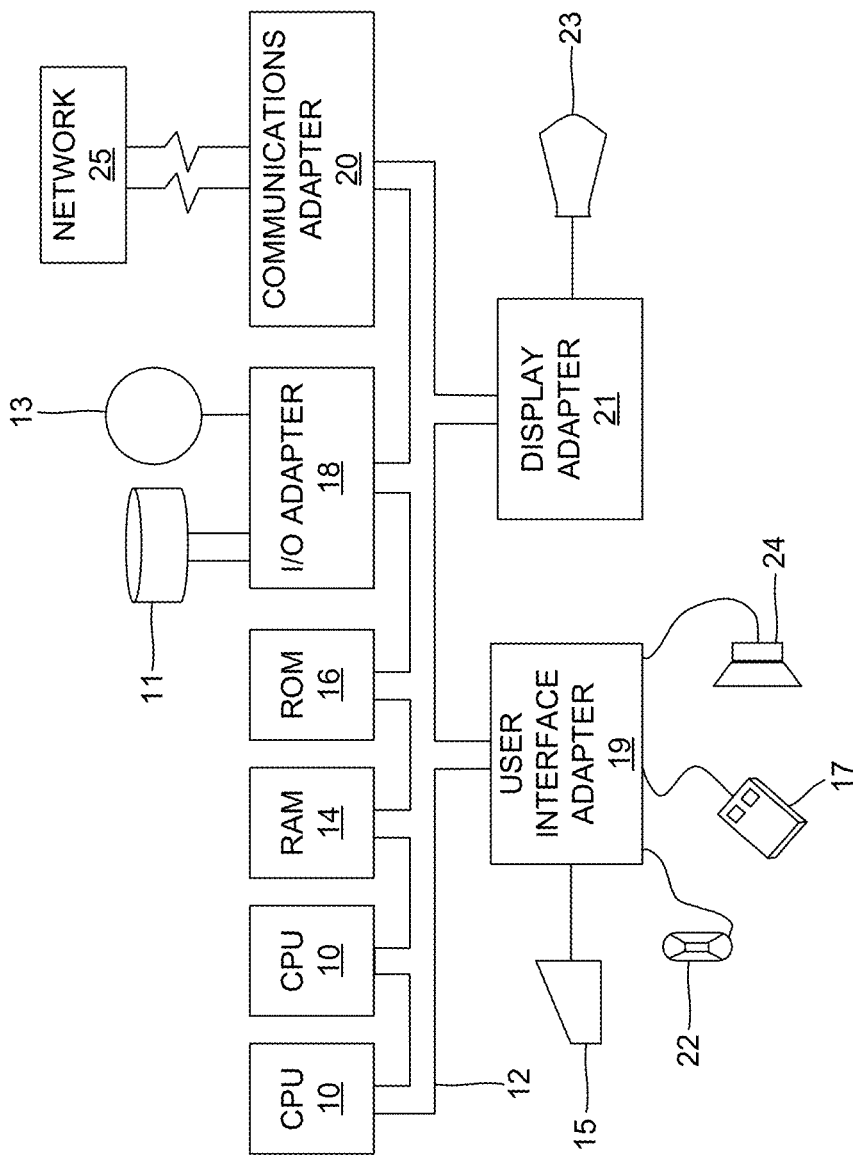

SYSTEM FOR REFERRAL MANAGEMENT

BACKGROUND

Technical Field

The embodiments herein generally relate to a care orchestration, and, more particularly, a system and method of referral and data management in the healthcare industry.

Description of the Related Art

Transfer of care of a patient from one health professional to another is known as a medical referral or referral. Large enterprise hospitals with a strong provider base send and receive thousands of referrals in and out of its network on a daily basis. Generally, referrals originate from a primary care provider, also known as a referring provider, and are sent to a specialist. Referrals play a critical role in ensuring that each patient gets the right care at the right time and under the right specialist. Referrals also greatly contribute to a hospital's revenue system. However, to balance revenue generation and quality care for patients, large hospitals face major hurdles while managing referrals and lose an estimated 55-65% of their revenue due to referral leakage. Referring providers and referral coordinators do not receive timely referral progress updates and are required to coordinate over multiple communication channels such as phone, email, direct message, website, and fax to complete the initiation of a single referral. They are also required to perform the insurance pre-authentication process which makes the referral management process highly tedious and time-consuming. The specialists, who receive referrals, face problems like consolidating referrals through various channels, incomplete paperwork and missed follow-ups. This results in referral leakage and productivity loss thus decreasing revenue. The patients are often burdened with communicating with multiple offices and get delayed appointments even after referral initiation. They miss their appointments and follow-ups due to improper or no reminders and notifications and are also forced to undergo repeat diagnostic tests due to lack of information or communication between the referring provider and the specialist.

Accordingly, there remains a need for a referral management system to consolidate referrals and its information from multiple sources, facilitates effective communication and exchange between key actors of a referral ecosystem and coordinates end to end referral process till referral closure.

SUMMARY

In view of foregoing, an embodiment herein provides a system for managing at least one referral and automatically performing at least one action based on the at least one referral in a health care-environment. The system includes a memory and a processor. The memory stores a database. The database includes referral information associated with the at least one referral. The processor is configured to: (i) enable the system to receive the at least one referral from at least one of (a) a referral provider via a referral provider device or (b) a user via a user device; (ii) perform a prioritization of the at least one referral by analysing the referral information associated with the at least one referral to automatically generate a referral queue; (iii) perform at least one of (a) retrieve the referral information associated with the at least one referral from the database by identifying the referral information associated with the at least one referral based on the referral queue or (b) automatically search and retrieve external information associated with the at least one referral from at least one external database when the at least one referral requires the external information associated with the at least one referral; (iv) determine the at least one action based on the at least one referral by populating at least one of template using at least one of (a) the referral information associated with the at least one referral or (b) the external information associated with the at least one referral; and (v) automatically enable at least one of (a) a specialist, (b) the referral provider or (c) the user to perform the at least one action based on the at least one referral by analysing the at least one template populated with the referral information associated with the at least one referral and the external information associated with the at least one referral.

In some embodiments, the processor is configured to automatically enable the specialist to perform at least one action on the at least one referral based on the priorities of the specialist. The referral information associated with the at least one referral is provided to the specialist to perform actions on the at least one referral. The referral information includes at least one of patient demographics, clinical information, clinical charts, a reason for a referral, details of a specialist or referral provider details. The at least one action includes at least one of (i) generate or customize at least one of workflow, a dynamic widget, self-guiding and surveys or a referral report that corresponds to the at least one referral and the referral provider; (ii) manage facility, plugin, template; (iii) import or export at least one of the referral information or the external information from various databases; (iv) schedule appointment request by coordinating with a specialist office and a patient; (v) generate a patient follow-up letter and mail the patient follow-up letter to a patient; (vi) communicate with the referral providers on additional information required on the referral and update the specialist office about the patient appointment; (vii) follow-up with the specialist office on the referral status; or (viii) validate the referral report and complete or close the referral.

In some embodiments, the processor is further configured to enable a communication between at least one of: the referral provider, at least one user or at least one specialist in the referral eco-environment. The system integrates with a communication tool to enable the communication.

In some embodiments, the processor is further configured to generate at least one automated customizable workflow based on a requirement associated with the at least one referral. The at least one of workflow includes triggering an automated notification, creating tasks, creating multiple statuses to determine a lifecycle of the at least one referral.

In some embodiments, the processor is further configured to transform the referral information and the external information into a predetermined format to store in the database. The referral information and the external information are imported and exported in databases. The external information includes at least one of patient information or insurance information.

In some embodiments, the processor is further configured to enable the user to generate dynamic widgets based on the requirement of the user and the referral. The dynamic widgets are generated based on user types. The user type includes operational data for (i) referral coordinators, (ii) staffs and (iii) overall practice performance data for at least one of management users or administrators.

In some embodiments, the processor is further configured to generate a report that corresponds to the at least one referral at a periodic instance using selected data from the referral information and the external information. The report includes an organizational report and a referral provider report. The selected data includes at least one of patient demographics, clinical information or a clinical chart, a reason for referral, a specialist name, the referral provider and their contact details and associated documents.

In some embodiments, the processor is further configured to perform at least one of (i) enable the user to set at least one configuration for the system, (ii) maintain facilities provided by an organization, (iii) manage user identities and access details to customize the report based on the requirement of the at least one referral, (iv) manage core data of the organization for automatically performing a plurality of actions based on the at least one referral, (v) automatically generate and run a workflow for each referral based on the requirement of the at least one referral, (vi) manage an update and new features of the system, (vii) improve a quality of the service by generating self-guiding and interactive online surveys which are needed for organizations, (viii) generate, maintain and control the templates of the system that is used for at least one of referral management or data management, (ix) generate customized lightweight components and modules based on the requirements to eliminate a need of scripts writing and enable the user to seamlessly add data, (x) define own roles and assigns on a need to know basis or (xi) import and export information of the referral associated with the referral provider, the plurality of patients and the one or more specialists. The at least one configuration includes at least one of date, time, title, color, logo, fonts or timeout. The facilities include at least one of a guest room, a cloakroom, or a vehicle parking. The user identities include at least one of password resets, creating and provisioning, blocking, deleting or credentials of a plurality of patients. The core data includes at least one of a specialty, insurance, Medications, Vitals, Allergies or Language of the organization. The processor is configured to monitor a process consistency, eliminating errors and problems due to lost or mishandled requests. The processor configured to enable installation, update and uninstall of applications with the system. The user access may be restricted on the basis of internal or external departments/facilities.

In some aspects, a method for managing at least one referral and automatically performing at least one action based on the at least one referral in a health care-environment. The method includes a steps of (i) receiving the at least one referral from at least one of (a) a referral provider via a referral provider device or (b) a user via a user device, (ii) performing a prioritization of the at least one referral by analysing the referral information associated with the at least one referral to automatically generate a referral queue, (iii) performing at least one of (a) retrieve the referral information associated with the at least one referral from the database by identifying the referral information associated with the at least one referral based on the referral queue or (b) automatically search and retrieve external information associated with the at least one referral from at least one external database when the at least one referral requires the external information associated with the at least one referral, (iv) determining the at least one action based on the at least one referral by populating at least one of template using at least one of (a) the referral information associated with the at least one referral or (b) the external information associated with the at least one referral and (v) automatically enable at least one of (a) a specialist, (b) the referral provider or (c) the user to perform the at least one action based on the at least one referral by analysing the at least one template populated with the referral information associated with the at least one referral and the external information associated with the at least one referral.

In some embodiments, the method includes automatically enabling the specialist to perform at least one action on the at least one referral based on the priorities of the specialist. The referral information associated with the at least one referral is provided to the specialist to perform actions on the at least one referral. The referral information includes at least one of patient demographics, clinical information, clinical charts, a reason for a referral, details of a specialist or referral provider details. The at least one action includes at least one of (i) generating or customizing at least one of workflow, a dynamic widget, self-guiding and surveys or a referral report that corresponds to the at least one referral and the referral provider, (ii) managing facility, plugin, template, (iii) importing or exporting at least one of the referral information or the external information from various database, (iv) scheduling appointment request by coordinating with a specialist office and a patient, (v) generating patient follow-up letter and mail the patient follow-up to a patient, (vi) communicating with the referral provider on additional information required on the referral and update the specialist office about the patient appointment, (vii) follow-up with the specialist office on the referral status or (viii) validating the referral report and complete or close the referral.

In some embodiments, the method includes enabling a communication between at least one of the referral provider, at least one user or at least one specialist in the referral eco-environment. The system integrates with a communication tool to enable the communication.

In some embodiments, the method includes generating at least one automated customizable workflow based on a requirement associated with the at least one referral. The at least one of automated customizable workflow includes triggering automated notification, creating tasks, creating multiple statuses to determine a lifecycle of the at least one referral.

In some embodiments, the method includes transforming the referral information and the external information into a predetermined format to store in the database. The referral information and the external information are imported and exported in databases. The external information includes at least one of patient information or insurance information.

In some embodiments, the method includes enabling the user to generate dynamic widgets based on the requirement of the user and the referral. The dynamic widgets are generated based on user types. The user type includes operational data for (i) referral coordinators, (ii) staffs and (iii) overall practice performance data for at least one of management users or administrators.

In some embodiments, the method includes generating a report that corresponds to the at least one referral at a periodic instance using selected data from the referral information and the external information. The report includes an organizational report and a referral provider report. The selected data includes at least one of patient demographics, a clinical information or a clinical chart, a reason for referral, a specialist name, the referral provider and their contact details and associated documents.

In some embodiments, the method includes at least one of (i) enabling the user to set at least one configuration for the system, (ii) maintaining facilities provided by an organization, (iii) managing user identities and access details to customize the report based on the requirement of the at least one referral, (iv) managing core data of the organization for automatically performing a plurality of actions based on the at least one referral, (v) automatically generating and run a workflow for each referral based on the requirement of the at least one referral, (vi) managing an update and new features of the system, (vii) improving a quality of the service by generating self-guiding and interactive online surveys which are needed for organizations, (viii) generating, maintain and control the templates of the referral management system that is used for at least one of referral management or data management, (ix) generating customized, lightweight components and modules based on the requirements to eliminate a need of scripts writing and enable the user to seamlessly add data, (x) defining own roles and assigns on a need to know basis or (xi) importing and exporting information of the referral associated with the referral provider, the one or more patients and the plurality of specialists. The processor is configured to enable installation, update and uninstall of applications with the system. The processor is configured to monitor a process consistency, eliminating errors and problems due to lost or mishandled requests. The core data includes at least one of a specialty, an insurance, Medications, Vitals, Allergies or Language of the organization. The user identities include at least one of password resets, creating and provisioning, blocking, deleting or credentials of a plurality of patients. The at least one configuration includes at least one of date, time, title, color, logo, fonts or timeout. An user access may restricted on a basis of internal or external departments/facilities. Facilities include at least one of a guest room, a cloakroom, or a vehicle parking.

These and other aspects of the embodiments herein will be better appreciated and understood when considered in conjunction with the following description and the accompanying drawings. It should be understood, however, that the following descriptions, while indicating preferred embodiments and numerous specific details thereof, are given by way of illustration and not of limitation. Many changes and modifications may be made within the scope of the embodiments herein without departing from the spirit thereof, and the embodiments herein include all such modifications.

BRIEF DESCRIPTION OF THE DRAWINGS

The embodiments herein will be better understood from the following detailed description with reference to the drawings, in which:

FIG. 8 illustrates a user interface view of a referral queue of FIG. 1 according to some embodiments herein;

FIG. 12 illustrates a schematic diagram of a hardware configuration of a computer architecture according to some embodiments herein.

DETAILED DESCRIPTION OF PREFERRED EMBODIMENTS

Figure 1:
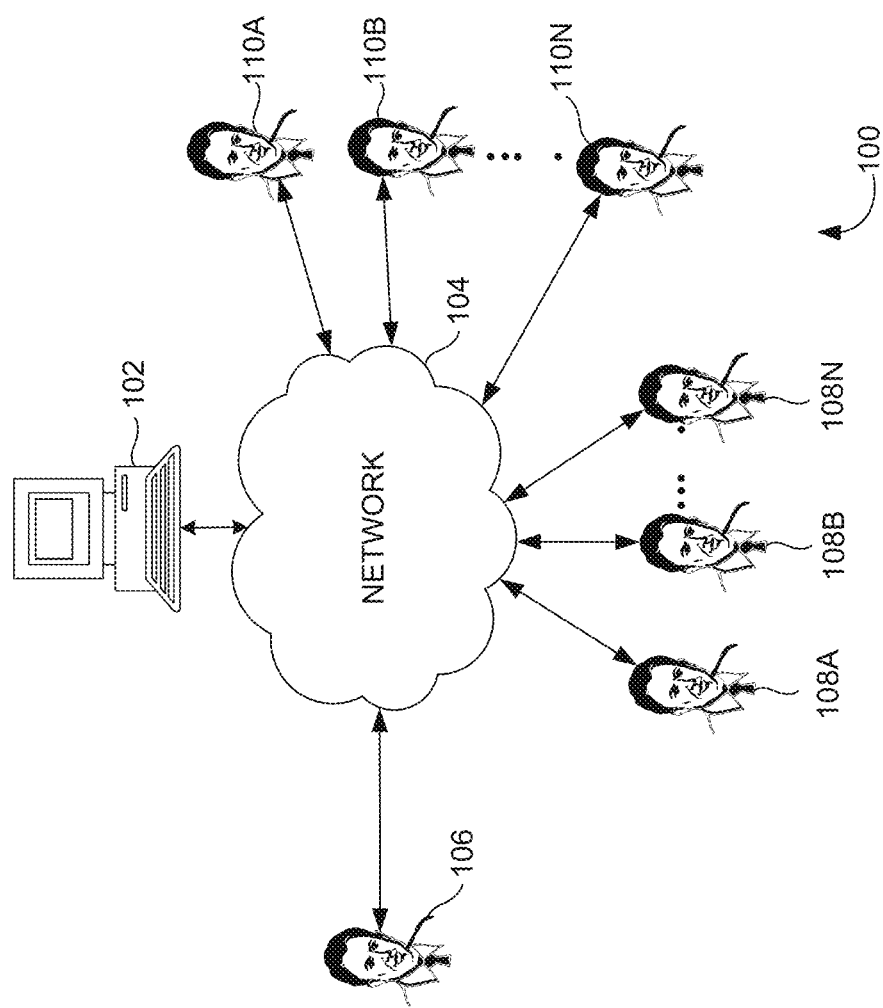
FIG. 1 is a block diagram that illustrates a system that manages referrals from reference provider, patient and recovers provider according to some embodiments herein.

The embodiments herein and the various features and advantageous details thereof are explained more fully with reference to the non-limiting embodiments that are illustrated in the accompanying drawings and detailed in the following description. Descriptions of well-known components and processing techniques are omitted so as to not unnecessarily obscure the embodiments herein. The examples used herein are intended merely to facilitate an understanding of ways in which the embodiments herein may be practiced and to further enable those of skill in the art to practice the embodiments herein. Accordingly, the examples should not be construed as limiting the scope of the embodiments herein.

As mentioned, there remains a need for a new tool to consolidate referrals from multiple sources, facilitate effective communication and exchange between key actors of a referral ecosystem and coordinate end to end referral process till referral closure. The embodiments herein achieve this by providing a system for referral management. Referring now to the drawings, and more particularly to FIGS. 1 through 12, where similar reference characters denote corresponding features consistently throughout the figures, there are shown preferred embodiments.

FIG. 1 is a block diagram 100 that illustrates a system that manages referrals from reference provider, patient and recovers provider according to some embodiments herein. The block diagram 100 includes the referral management system 102, a network 104, a referral provider 106, one or more patients 108A-N and one or more specialists 110A-N. The referral management system 102 extracts referral information from the reference provider 106. The referral information includes patient demographics, clinical information or charts, the reason for referral, a specialist name, referral provider 106 and their contact details and associated documents. In some embodiments, the referral provider 106 communicated with the referral management system 102 through the network 104. The referral management system 102 communicates the one or more patients 108A-N and the one or more specialists 110A-N through the network 104. In some embodiments, the network 104 is a wired network. In some embodiments, the network 104 is a wireless network. The referral management system 102 automatically identifies an order for referrals from the referral provider 106 and places the referrals in a queue. In some embodiments, one or more patients 108A-N request a referral. The referral management system 102 validates the requested referral to identify a type of requested referral using the referral information and co-ordinates the requested referral with the referral provider 106. The referral provider 106 determines a specialist 110A from the one or more specialists 110A-N based on the identified referral type. In some embodiments, the referrals are initiated by the referral provider 106. The referral provider 106 includes at least one of Primary Care Providers, or front desk persons on behalf of the Primary Care Providers. The referral management system 102 communicates the referrals to the determined specialist with patient information and referral information. The referral management system 102 communicates the referrals to a patient 108A using one or more channels. In some embodiments, the one or more channels include at least one of an e-fax, a phone, a direct messaging, an Electronic Medical Report (EMR), an Electronic mail, a website, a physical Form or a patient's walk-in. The referral management system 102 provides periodical reminders for the referral to both the specialist and the patient 108A. The referral management system 102 includes a database with information provided by the specialist on the referrals. In some embodiments, each action performed by the specialist on the patient 108A is updated in the database of the referral management system 102. The referral management system 102 generates a referral report for the referral provider 106 in a predefined format using the information stored in the database regarding the actions associated with the referrals. The referral management system 102 enables the referral provider 106 to perform one or more actions based on the report generated by the referral management system 102. In some embodiments, the one or more actions are executed based on a practice workflow when the referral provided to the specialist. The one or more actions include at least one of (i) insurance pre-authorization, (ii) schedule appointment request by coordinating with a specialist office and the patient 108A, (iii) generate patient follow-up letter and mail the patient follow-up letter to the patient 108A, (iv) communicate with the referral provider 106 on additional information required on the referral and update the specialist office about the patient appointment, (v) follow-up with the specialist office on the referral status or (vi) validate the referral report and complete or close the referral. In some embodiments, the insurance pre-authorization has initiated a process of checking insurance eligibility for the patient 108A when the patient 108A is treated by this specialist for claiming the insurance from insurance companies or Payers. The insurance eligibility checking process is automated in the referral management system using Application Programming Interface integration that automatically pre-populating the patient information in the respective electronic-forms and automatically submits insurance claim request in the respective websites of the insurance companies or the Payers through online).

Figure 2:
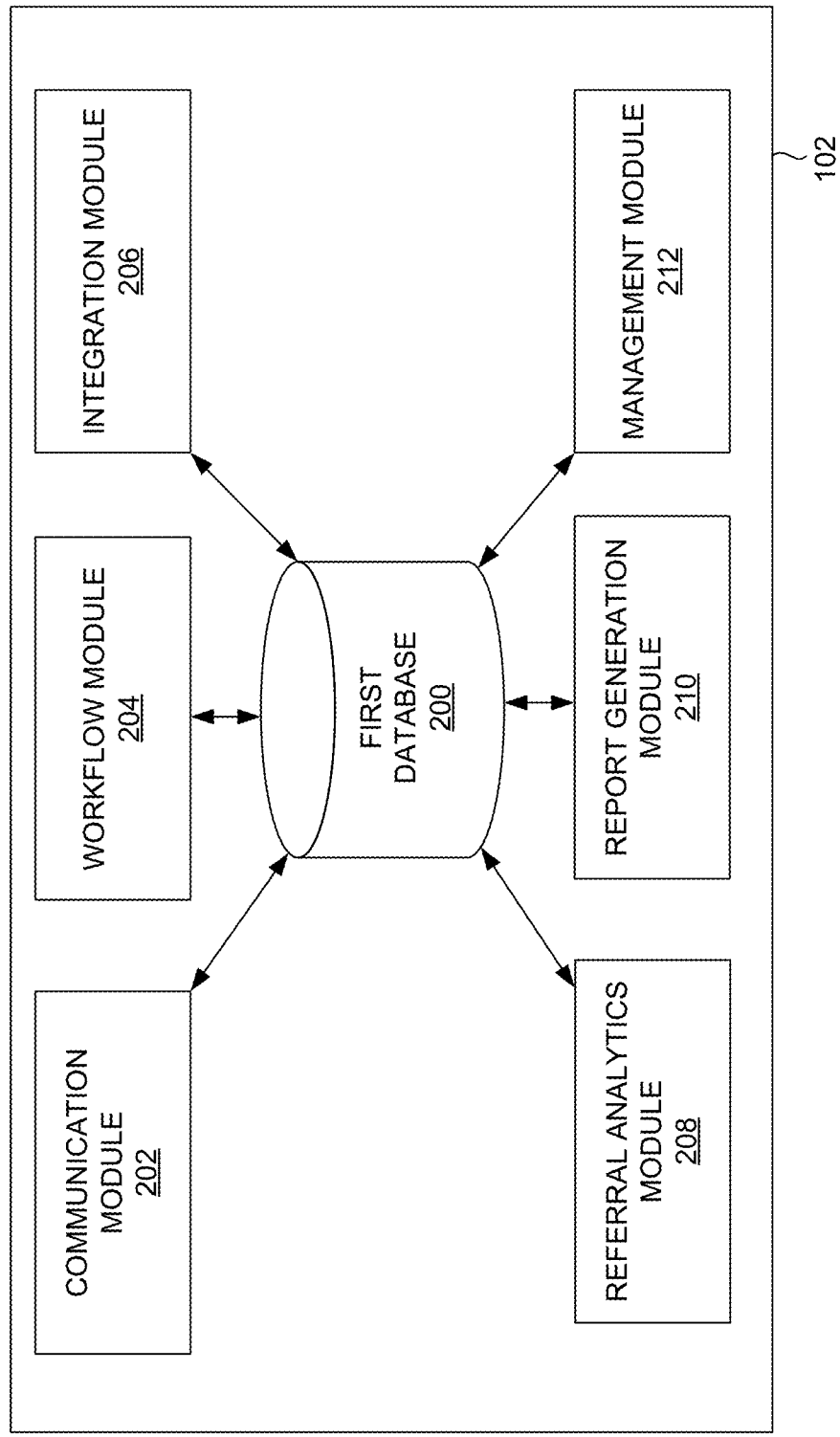
FIG. 2 is an exploded view of the referral management system of FIG. 1 according to some embodiments herein.

With reference to FIG. 1, FIG. 2 is an exploded view of the referral management system 102 according to some embodiments herein. The referral management system 102 includes a first database 200, a communication module 202, a workflow module 204, an integration module 206, a referral analytics module 208, a report generation module 210 and a management module 212. The communication module 202 enables the referral provider 106, the one or more patients 108A-N and of the one or more specialists 110A-N to communicate with each other based on preferences. In some embodiments, the communication module 202 integrates a communication tool with the referral management system 102 to enable the communication between at least one of the referral provider 106, one or more patients 108A-N and the one or more specialists 110A-N. The communication tool includes at least one of synchronous or asynchronous messaging, Short Message Service (SMS), Audio/Video/Text Chat, E-mail, E-Fax or Soft calling.

The workflow module 204 generates one or more automated customizable workflows or approval process based on requirements associated with referrals. In some embodiments, a automated customizable workflow is generated based on a standard predetermined template. The one or more automated customizable workflows include a triggering automated notification, creating tasks, creating multiple statuses to provide an effective referral lifecycle. In some embodiments, the one or more automated customizable workflows are generated for an individual or a group of users for defined function. In some embodiments, the automated customizable workflow of the referral includes referral inbound, referral outbound and referral in-out bound. The integration module 206 converts patient information into a predetermined format to store the patient information in the first database 200. In some embodiments, the patient information in the form of Electronic Medical Report (EMR) or an external application. In some embodiments, the integration module 206 exports and imports the patient information from various databases. In some embodiments, the imported information stored in the first database 200 is converted into a universally accepted format.

The referral management system 102 further includes a custom report module (not shown in drawings) that enables at least one of the referral provider 106, the one or more patients 108A-N or the one or more specialists 110A-N to customize the information available in the first database 200. In some embodiments, the integration module 206 adapts with at least one of HL7 interface, API, CCDA or file-based. The referral analytics module 208 enables a user to create dynamic widgets based on the requirement of the user. In some embodiments, the dynamic widgets are created based on types of the user such as operational data for referral coordinators, staffs and overall practice performance data for management users or administrators.

The report generation module 210 generates reports that includes at least one of an organizational report, referral reports or a referral provider report based on the referrals. In some embodiments, the reports are generated for periodical instance with selected data. The organizational report includes at least one details of a referral IN or a referral OUT of at least one of the organizations or departments. The referral provider report includes at least one of detailed information about referral activity or a specific referral provider. In some embodiments, the report generation module 210 enables the user to filter data available in the reports based on at least one of referral types, a referral direction or a referral status. The reports may download in Portable Document Format (PDF), Excel or Comma-separated values (CSV) format. The management module 212 enables at least one of the referral provider 106, the one or more patients 108A-N or the one or more specialists 110A-N to customize the reports based on the requirement of the referrals. The management module 212 provides a template and/or a filter field to the user to enable the user to generate a customized report. In some embodiments, the management module 212 provides an editable document (Example: Portable Document Format (PDF)) for at least one of the referral provider 106, the one or more patients 108A-N or the one or more specialists 110A-N.

Figure 3:
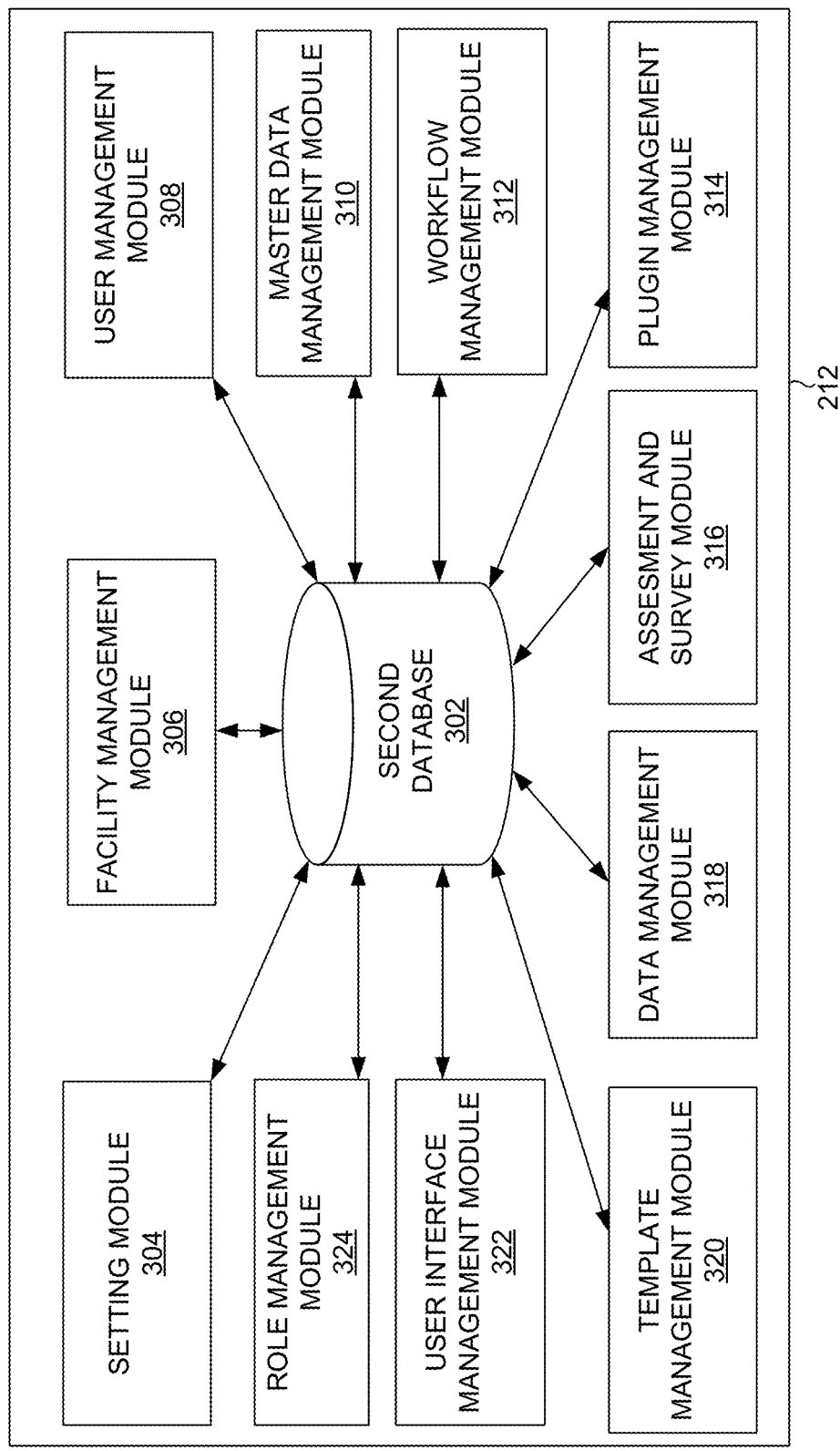
FIG. 3 is a block diagram of a management module of the referral management system of FIG. 2 according to some embodiments herein.

With reference to FIG. 1 and FIG. 2, FIG. 3 is a block diagram of the management module 212 of the referral management system 102 according to some embodiments herein. The management module 212 includes a second database 302, a setting module 304, a facility management module 306, a user management module 308, a master data management module 310, a workflow management module 312, a plugin management module 314, an assessment and survey module 316, a data management module 318, a template management module 320, a user interface management module 322 and a role management module 324. The setting module 304 enables a user to set at least one of the date, time, title, color, logo, fonts or timeout configurations for the referral management system 102. The facility management module 306 maintains facilities (e.g. guest room, clock room, vehicle parking, etc.) provided by an organization.

The user management module 308 manages user identities and access details. The user identities may include at least one of password resets, creating and provisioning, blocking, deleting or credentials of the patient. The master data management module 310 maintains core data of the organization that includes at least one of specialty, Insurance, Medications, Vitals, Allergies or Language, etc. of the organization. The master data management module 310 coordinates the core data in a common point of reference. The workflow management module 312 automatically generates and runs the workflow for each referral based on the requirement of the referrals. The workflow management module 312 enables the user to introduce or rearrangement of new data fields, add new status and introduce standard components. In some embodiments, the workflow management module 312 monitors process consistency, eliminating errors and problems due to lost or mishandled requests. The plugin management module 314 manages an update and new features of the referral management system 102. In some embodiments, a plugin with at least one of EMR's, schedulers, online fax, phone, email and cloud computing.

The plugin management module 314 enables installation, update and uninstall of applications with the referral management system 102. The assessment and survey module 316 generates self-guiding and interactive online surveys which are needed for organizations to improve the quality of service. In some embodiments, the assessment and survey module 316 improve the surveying process by reducing the surveys by adding known demographics and avoiding survey fatigue. The data management module 318 imports and exports information associated with the referral provider 106, the one or more patients 108A-N and the one or more specialists 110A-N. In some embodiments, the data management module 318 imports data from any CSV file. The template management module 320 generates, maintains and controls templates of the referral management system 102 that is used for at least one of referral management or data management. In some embodiments, the template management module 320 includes an organized and structural template library to amend, store find and manage the templates. The user interface management module 322 generates customized, lightweight components and modules based on the requirements. In some embodiments, the user interface management module 322 eliminates a need of scripts writing and enables the user to seamlessly add data to them. The role management module 324 defines own roles and assigns on a need to know basis. In some embodiments, an user access may be restricted on a basis of internal or external departments/facilities. The roles may be customizable and to be aligned with the organizational structure.

Figure 4:
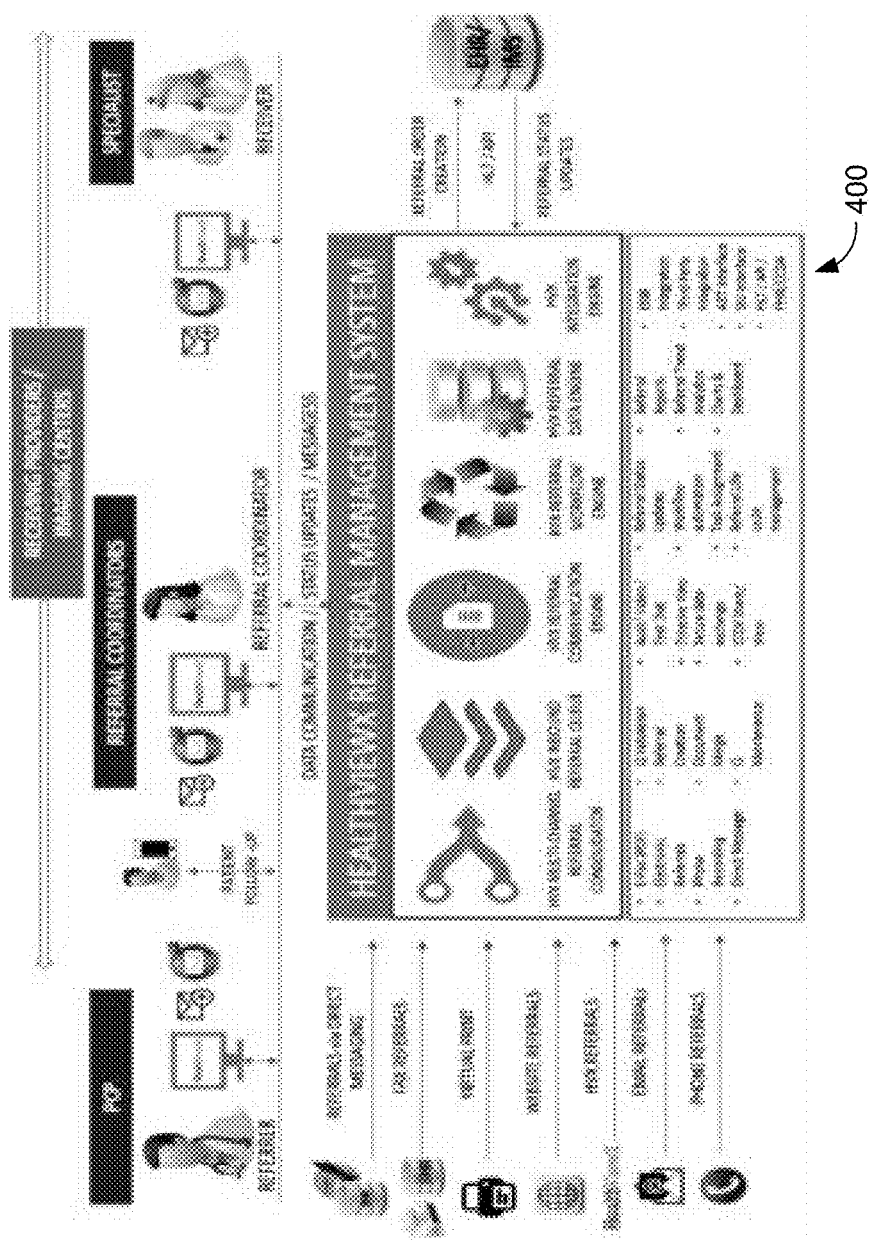
FIG. 4 illustrates a user interface view of an inbound referring practice of the referral management system according to some embodiments herein.

With reference to FIG. 1 and FIG. 2, FIG. 4 illustrates a user interface view 400 of an inbound referring practice of the referral management system 102 according to some embodiments herein. The referral inbound may implement within an organization, e.g. imaging center, labs, etc. The referral may receive from at least one of Fax, Email, Direct Message, and Phone and through Online forms on a website of the organization. The referral management system 102 integrates the referral and placed in a consolidated referral queue. The referral provider 106 validates and processes the referrals with the one or more specialists 110A-N. In some embodiments, the referral management system 102 uploads the reports of the referrals to the first database 202 after consultation and enables the referral provider 106 to access the reports.

Figure 5:
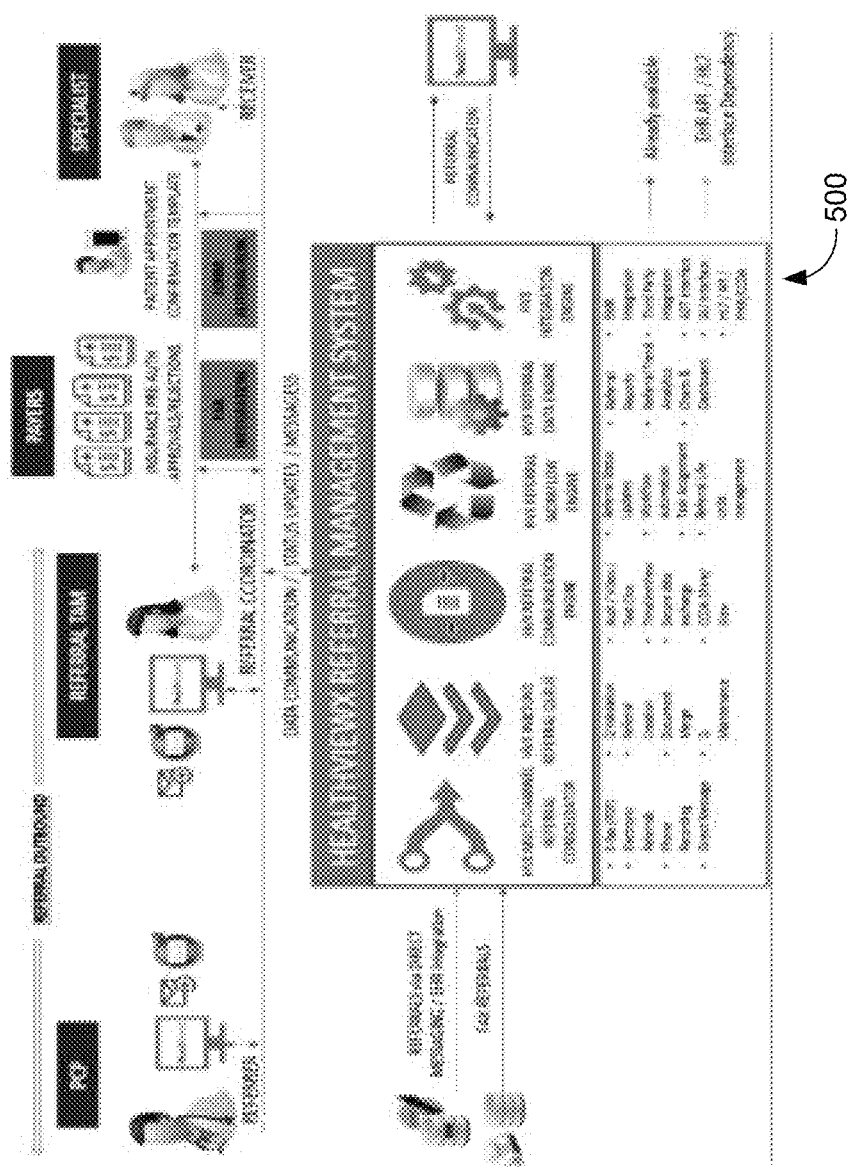
FIG. 5 illustrates a user interface view of an outbound referring practice of the referral management system according to some embodiments herein.

With reference to FIG. 1 and FIG. 2, FIG. 5 illustrates a user interface view 500 of an outbound referring practice of the referral management system 102 according to some embodiments herein. The referral outbound may implement with one or more hospitals, e.g. community hospitals, primary care centers, etc. The referrals are provided to specialty centers to process the referrals. The referral management system 102 enables the referral provider 106 to create the referrals to the one or more specialists 110A-N. In some embodiments, the one or more specialists 110A-N choose the mode for receiving the referral. The referral management system 102 places the referrals in a queue which manually merged with a respective specialist or the referral provider 106.

Figure 6:
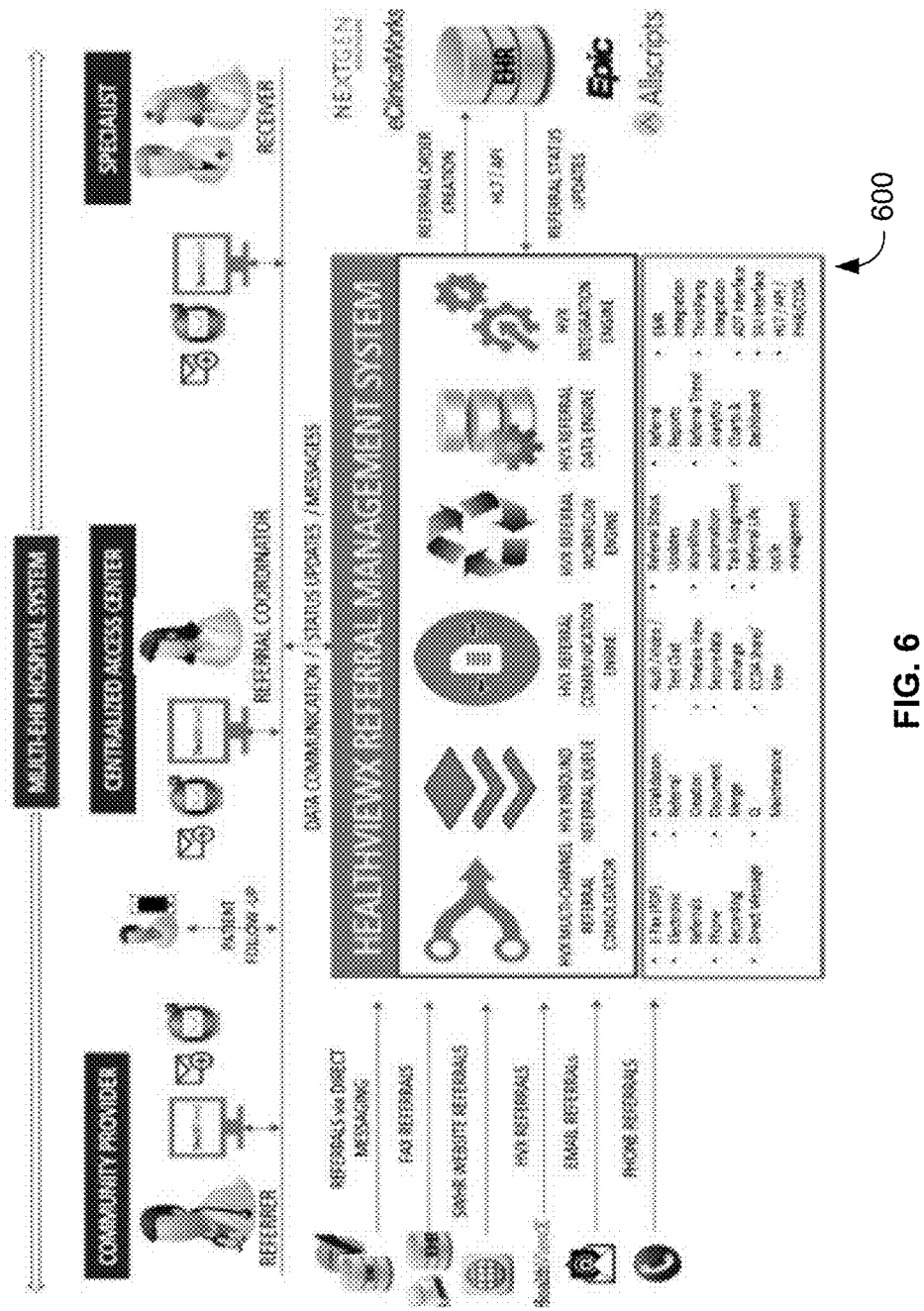
FIG. 6 illustrates an exemplary view of in-out bound referring practice of the referral management system according to some embodiments herein.

With reference to FIG. 1 and FIG. 2, FIG. 6 illustrates a user interface view 600 of an in-out bound referring practice of the referral management system 102 according to some embodiments herein. The in-out bound referring may implement with enterprise hospitals which facilitates both sending and receiving the referrals by a centralized referral coordination team. In some embodiments, the referrals are created by a primary care provider (PCP) in their EMRs are automatically created in the referral management system 102 with the help of the integration module 206. In some embodiments, the integration module 206 enables the referral provider 106 to process an insurance pre-authorization, assigns the specialist 110 and coordinate end to end referral process till referral closure. In some embodiments, the referral management system 102 uses custom built modules and components based on the requirement.

Figure 7:
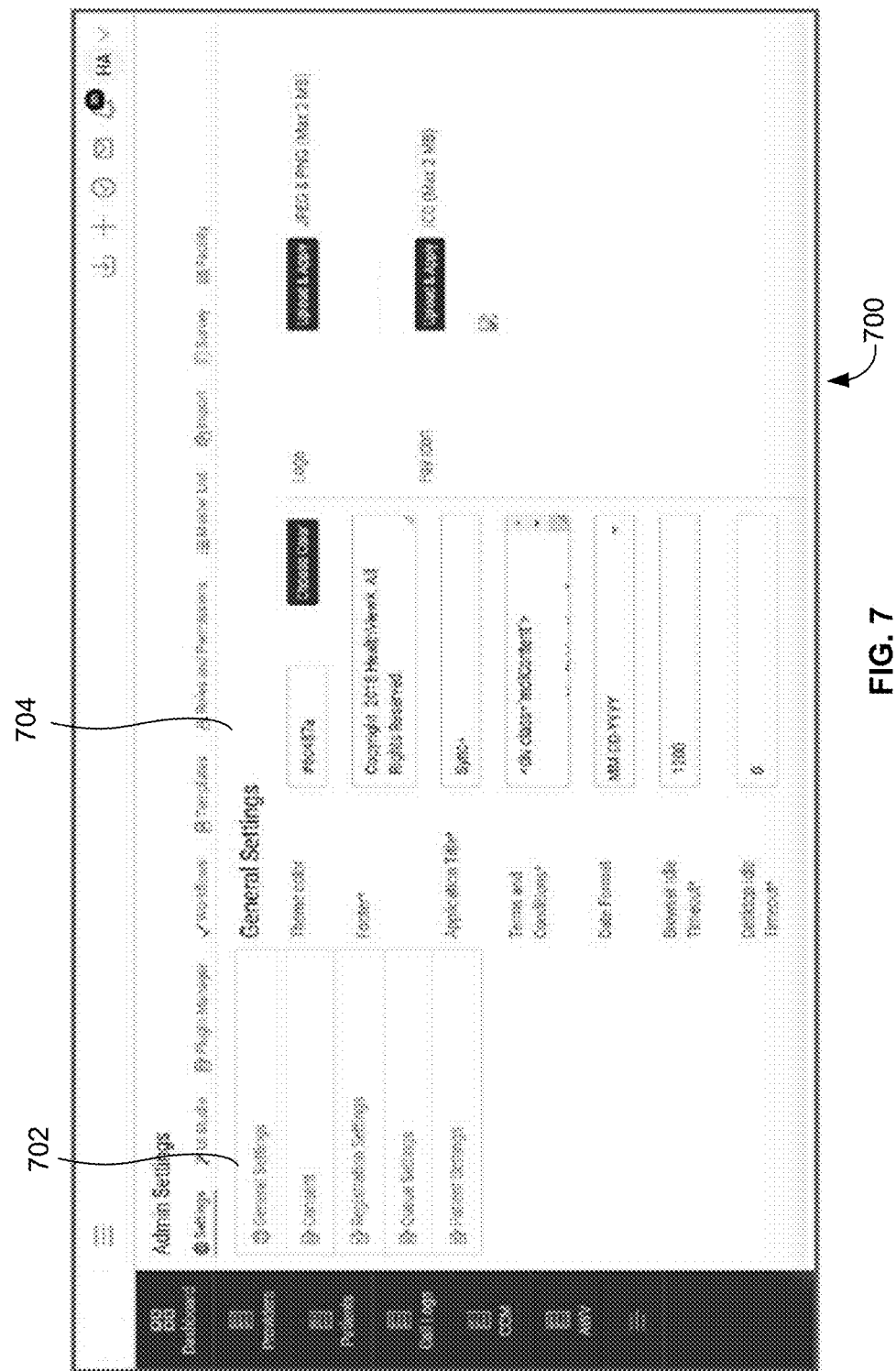
FIG. 7 illustrates a user interface view of a setting module of FIG. 3 according to some embodiments herein.

With reference to FIG. 1 and FIG. 2, FIG. 7 illustrates a user interface view 700 of the setting module 304 of FIG. 3 according to some embodiments herein. The user interface view 700 includes a settings tab 702 and a setting configuration tab 704. An admin may choose a type of settings to configure the referral management system 102 based on the requirement. The setting configuration tab 704 enables the admin to configure at least one of the date, time, title, color, logo, fonts or timeout configurations for the referral management system 102.

Figure 8:
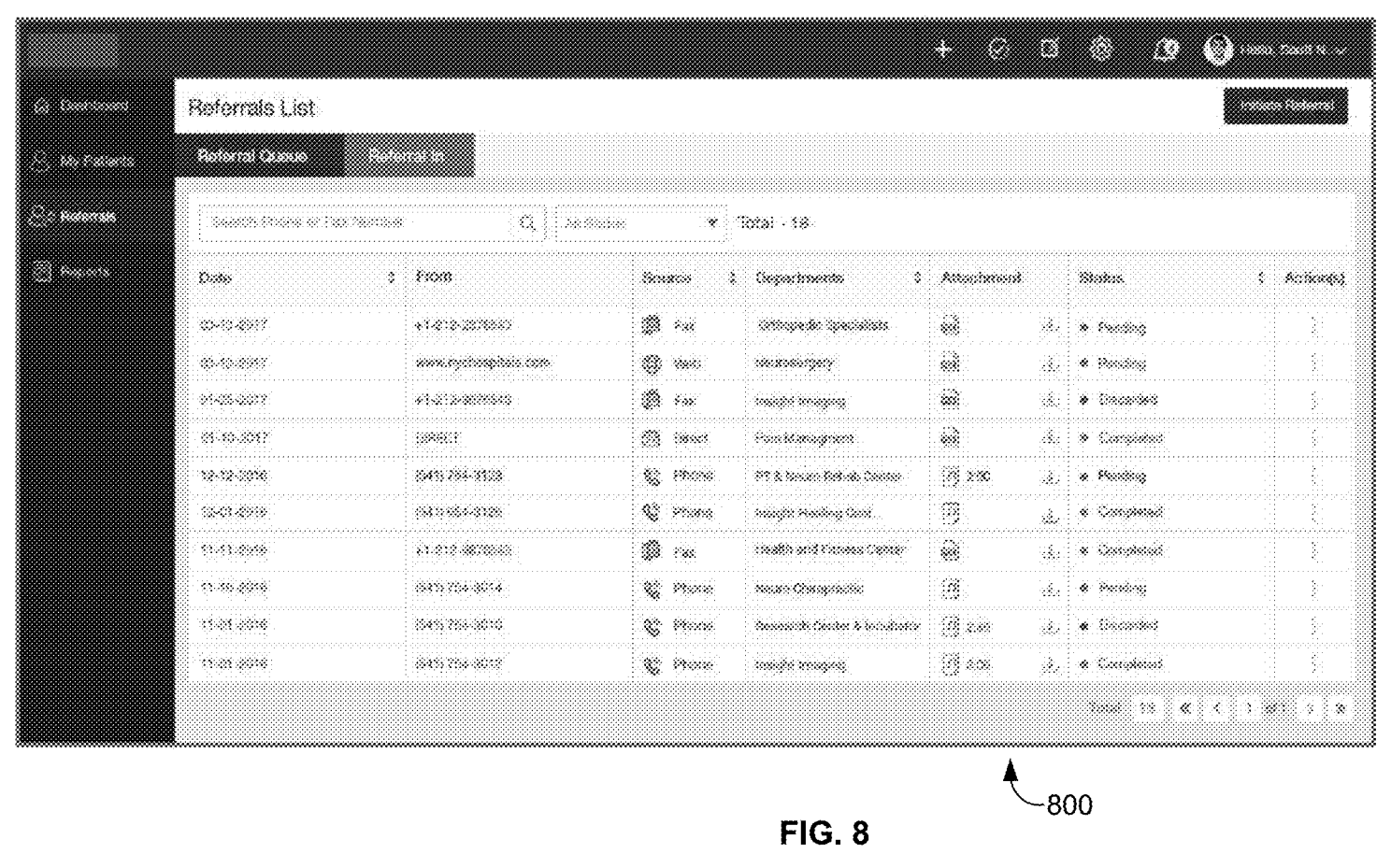

With reference to FIG. 1 and FIG. 2, FIG. 8 illustrates a user interface view 800 of a referral queue of FIG. 1 according to some embodiments herein. The user interface view 800 includes information associated with the referrals. In some embodiments, the information associated with the referrals includes at least one of a date, a source, a department, documents or attachments, status, from address details or action to be done. The referrals may be queued with a latest referral as first and an old referral as last, which can be modified with a sorting option. The source of receiving the referrals may include any of fax, web, direct, or phone, and the corresponding sender information can be included in from address details section of the user interface view 800. The status may include any of pending, discarded, or completed, which can be modified with a sorting option, as per user convenience. The user interface view 800 includes an initiate referral option that enables the specialist to provide the referrals.

Figure 9:
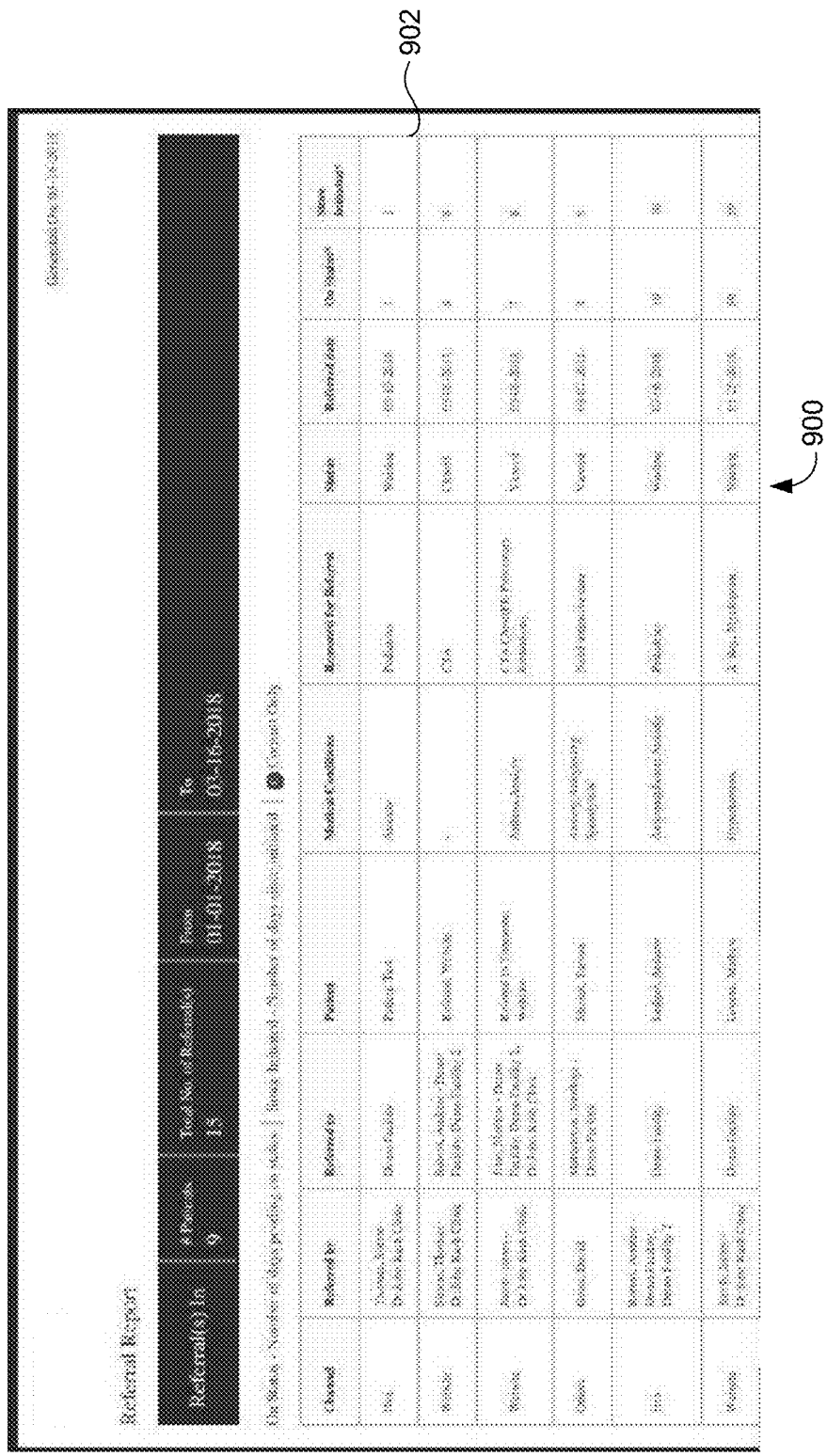
FIG. 9 illustrates a user interface view of referral reports of FIG. 1 according to some embodiments herein.
Figure 10A:
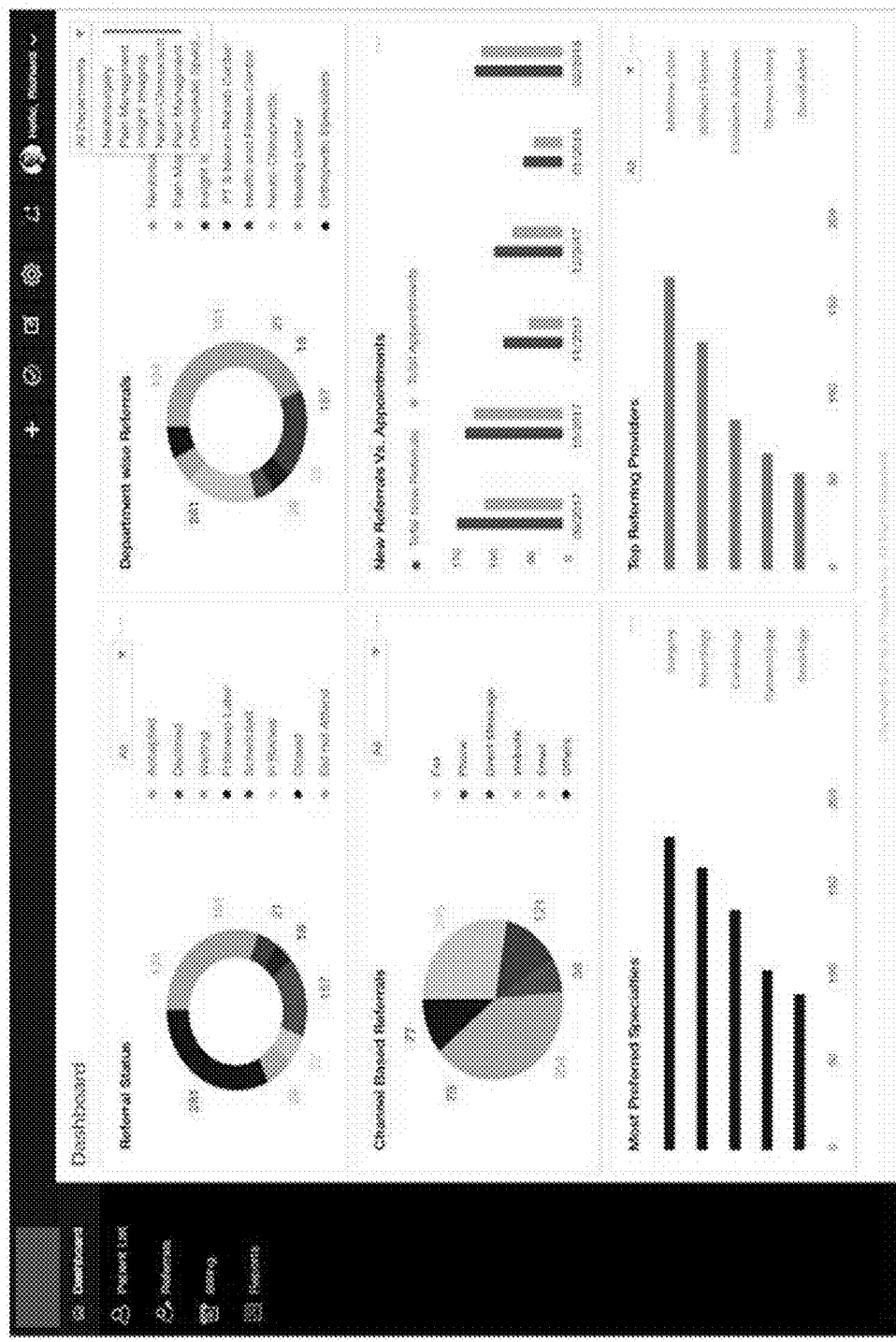
FIGS. 10A and 10B illustrate a user interface views of customized dashboards of FIG. 1 according to some embodiments herein.
Figure 10B:
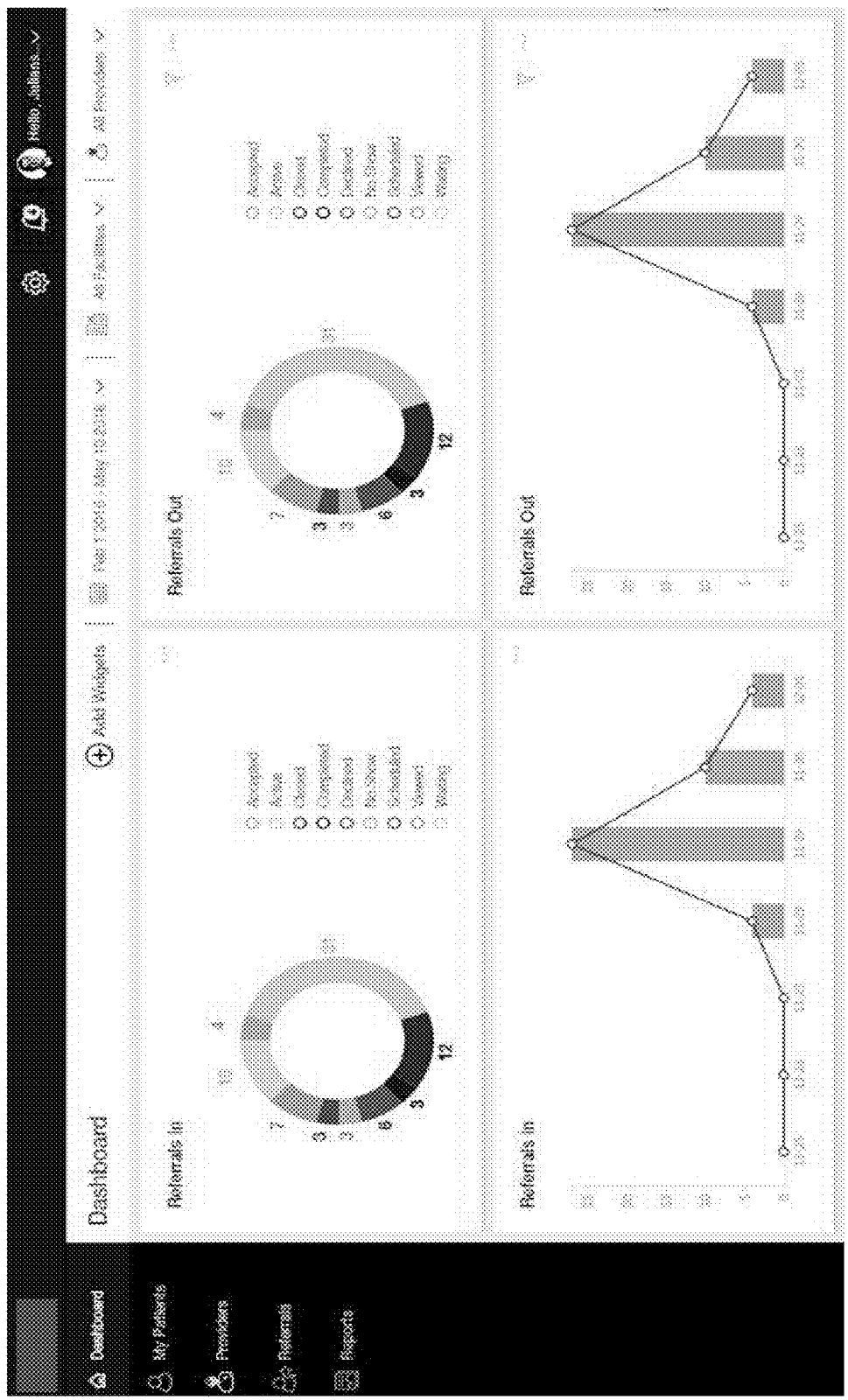

With reference to FIG. 1 and FIG. 2, FIG. 9 illustrates a user interface view 900 of referral reports of FIG. 1 according to some embodiments herein. The user interface view 900 includes timely monitored data populated in a report table 902. In some embodiments, the timely monitored data includes at least one of a referral source address, a referral destination address, patient name, medical conditions, remarks or status, referred date, on status, and since initiated. The on status shows the number of days pending on status, and the since initiated shows the number of days since initiated that particular referral. The referral queue may be sorted based on the on status and the since initiated data.

With reference to FIG. 1 and FIG. 2, FIGS. 10A and 10B illustrate user interface views of a customized dashboard of FIG. 1 according to some embodiments herein. The customizable dashboard includes information associated with the referrals.

Figure 11:
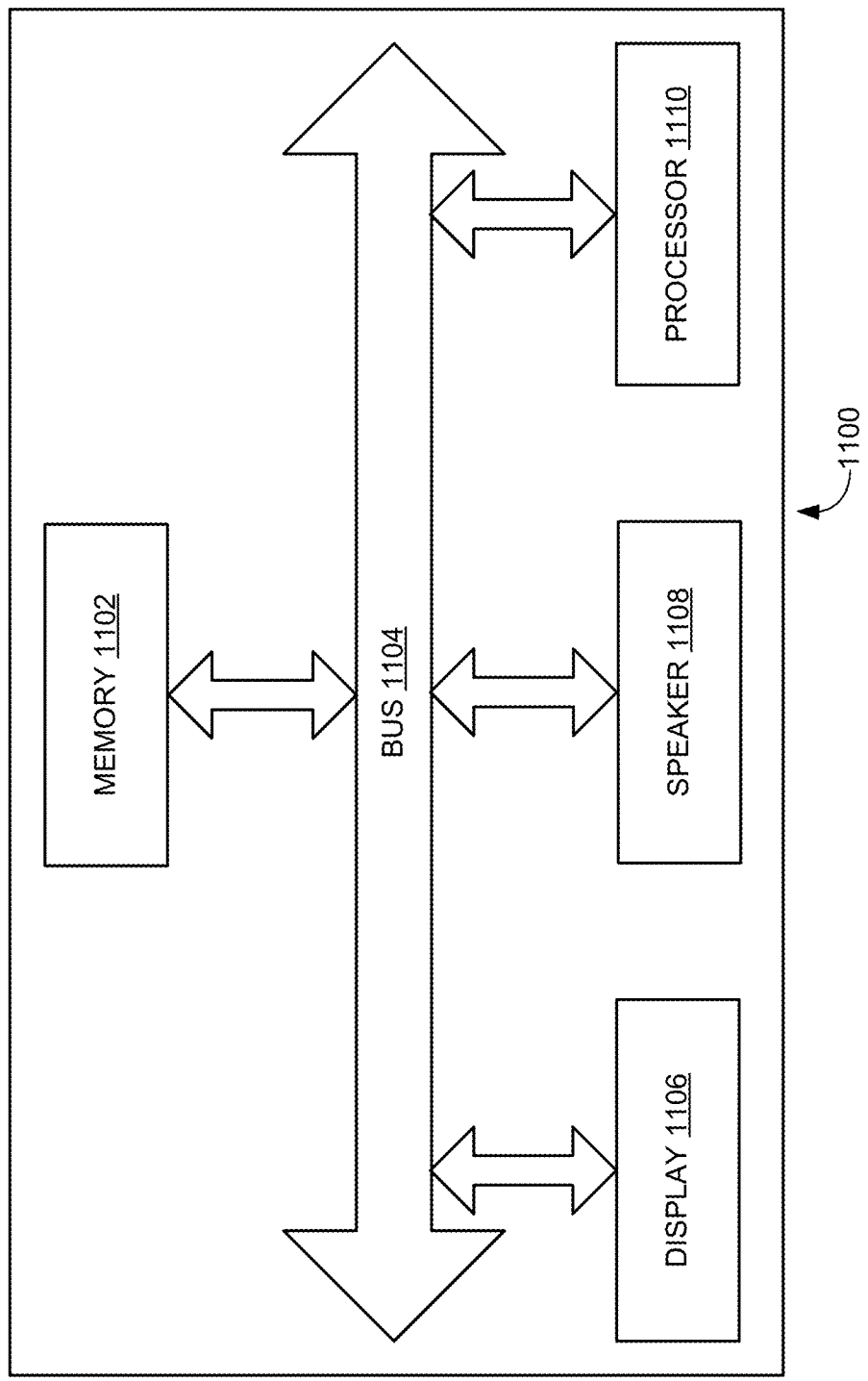
FIG. 11 illustrates an exploded view of a receiver of FIG. 1 according to some embodiments herein.

With reference to FIG. 1 and FIG. 2, FIG. 11 illustrates an exploded view of a receiver 1100 of FIG. 1 having a memory 1102 having a set of instructions, a bus 1104, a display 1106, a speaker 1108, and a processor 1110 capable of processing the set of instructions to perform any one or more of the methodologies herein, according to some embodiments herein. The processor 1110 may also enable digital content to be consumed in the form of a video for output via one or more displays or audio for output via speaker and/or earphones 1108. The processor 1110 may also carry out the methods described herein and in accordance with the embodiments herein.

Digital content may also be stored in the memory 1102 for future processing or consumption. The memory 1102 may also store program specific information and/or service information (PSI/SI), including information about digital content (e.g., the detected information bits) available in the future or stored from the past. A user of the receiver 1100 may view this stored information on display 1106 and select an item of for viewing, listening, or other uses via input, which may take the form of a keypad, scroll, or another input device (s) or combinations thereof. When digital content is selected, the processor 1110 may pass information. The content and PSI/SI may be passed among functions within the receiver using the bus 1104.

The techniques provided by the embodiments herein may be implemented on an integrated circuit chip (not shown). The chip design is created in a graphical computer programming language, and stored in a computer storage medium (such as a disk, tape, physical hard drive, or virtual hard drive such as in a storage access network). If the designer does not fabricate chips or the photolithographic masks used to fabricate chips, the designer transmits the resulting design by physical means (e.g., by providing a copy of the storage medium storing the design) or electronically (e.g., through the Internet) to such entities, directly or indirectly.

The stored design is then converted into the appropriate format (e.g., GDSII) for the fabrication of photolithographic masks, which typically include multiple copies of the chip design in question that are to be formed on a wafer. The photolithographic masks are utilized to define areas of the wafer (and/or the layers thereon) to be etched or otherwise processed.

The resulting integrated circuit chips can be distributed by the fabricator in raw wafer form (that is, as a single wafer that has multiple unpackaged chips), as a bare die, or in a packaged form. In the latter case, the chip is mounted in a single chip package (such as a plastic carrier, with leads that are affixed to a motherboard or other higher level carrier) or in a multichip package (such as a ceramic carrier that has either or both surface interconnections or buried interconnections). In any case, the chip is then integrated with other chips, discrete circuit elements, and/or other signal processing devices as part of either (a) an intermediate product, such as a motherboard, or (b) an end product. The end product can be any product that includes integrated circuit chips, ranging from toys and other low-end applications to advanced computer products having a display, a keyboard or other input device, and a central processor. The embodiments herein can take the form of, an entire hardware embodiment, an entire software embodiment or an embodiment including both hardware and software elements. The embodiments that are implemented in software include but are not limited to, firmware, resident software, microcode, etc. Furthermore, the embodiments herein can take the form of a computer program product accessible from a computer-usable or computer-readable medium providing program code for use by or in connection with a computer or any instruction execution system. For the purposes of this description, a computer-usable or computer readable medium can be any apparatus that can comprise, store, communicate, propagate, or transport the program for use by or in connection with the instruction execution system, apparatus, or device.

The medium can be an electronic, magnetic, optical, electromagnetic, infrared, or semiconductor system (or apparatus or device) or a propagation medium. Examples of a computer-readable medium include a semiconductor or solID state memory, magnetic tape, a removable computer diskette, a random access memory (RAM), a read-only memory (ROM), a rigID magnetic disk and an optical disk. Current examples of optical disks include compact disk-read only memory (CD-ROM), compact disk-read/write (CD-R/W) and DVD.

A data processing system suitable for storing and/or executing program code will include at least one processor coupled directly or indirectly to memory elements through a system bus. The memory elements can include local memory employed during actual execution of the program code, bulk storage, and cache memories which provide temporary storage of at least some program code in order to reduce the number of times code must be retrieved from bulk storage during execution.

Input/output (I/O) devices (including but not limited to keyboards, displays, pointing devices, remote controls, etc.) can be coupled to the system either directly or through intervening I/O controllers. Network adapters may also be coupled to the system to enable the data processing system to become coupled to other data processing systems or remote printers or storage devices through intervening private or public networks. Modems, cable modem and Ethernet cards are just a few of the currently available types of network adapters.

With reference to FIG. 1 and FIG. 2, FIG. 12 is a schematic drawing illustrates a hardware configuration of computer architecture in accordance with the embodiments herein. The computer architecture includes at least one processor or central processing unit (CPU) 10. The CPUs 10 are interconnected via system bus 12 to various devices such as a random access memory (RAM) 14, read-only memory (ROM) 16, and an input/output (I/O) adapter 18. The I/O adapter 18 can connect to peripheral devices, such as disk units 11 and tape drives 13, or other program storage devices that are readable by the system. The system can read the inventive instructions on the program storage devices and follow these instructions to execute the methodology of the embodiments herein.

The system 100 further includes a user interface adapter 19 that connects a keyboard 15, mouse 17, speaker 24, microphone 22, and/or other user interface devices such as a touch screen device (not shown) or remote control to the bus 12 to gather user input. Additionally, a communication adapter 20 connects the bus 12 to a data processing network 25, and a display adapter 21 connects the bus 12 to a display device 23 which may be embodied as an output device such as a monitor, printer, or transmitter, for example.

The referral management system 102 connected with the referral provider 106, the plurality of patients 108A-N and the plurality of specialist 110 A-N through the network 104. The referral management system 102 automatically identifies the order for the referrals and places in a queue. The referral management system 102 validates the requested referral to identify a referral type using the referral information and co-ordinates the referral with the referral provider 106. The referral provider 106 determines the specialist 110 from the plurality of specialists 110A-N based on the referral type. The referral management system 102 communicates the referrals to the determined specialist 110 with the patient information and referral information. The referral management system 102 communicates the referrals to the patient using the plurality of channels. The referral management system 102 provides a periodical reminder for the referral to both the specialist 110 and the patient 108. The referral management system 102 updated the first database 200 with information provided by the specialist 110 on referrals. The referral management system 102 generates reports for the referral provider 106 in the predefined format using the information stored in the first database 200 regarding the actions associated with referrals.

The foregoing description of the specific embodiments will so fully reveal the general nature of the embodiments herein that others can, by applying current knowledge, readily modify and/or adapt for various applications such specific embodiments without departing from the generic concept, and, therefore, such adaptations and modifications should and are intended to be comprehended within the meaning and range of equivalents of the disclosed embodiments. It is to be understood that the phraseology or terminology employed herein is for the purpose of description and not of limitation. Therefore, while the embodiments herein have been described in terms of preferred embodiments, those skilled in the art will recognize that the embodiments herein can be practiced with modification within the scope.

What is claimed is:

1. A system for managing at least one referral and automatically generating and prioritizing a referral queue to process follow-up and close the at least one referral in a health care-environment, the system comprising:
   a memory that stores a database, wherein the database includes referral information associated with the at least one referral; and
   a processor that is configured to:
      enable the system to receive the at least one referral from at least one of (i) a referral provider via a referral provider device or (ii) a user via a user device;
      validate the at least one referral to identify a type of the referral and communicate to the referral provider;
      receive at least one specialist determined by the referral provider based on the type of the at least one referral;
      communicate the at least one referral to the at least one specialist;
      perform a prioritization based on requirements of the at least one referral by analysing the referral information associated with the at least one referral to automatically generate the referral queue, wherein the referral information comprises at least one of patient demographics, clinical information, clinical charts, a reason for a referral, details of a specialist or referral provider details, wherein the referral information associated with the at least one referral is retrieved from the database based on the referral queue, and external information associated with the at least one referral is automatically searched and retrieved from at least one external database when the at least one referral requires the external information associated with the at least one referral;
      determine the at least one action based on the requirements of the at least one referral by generating a report that populates a template using at least one of (i) the referral information associated with the at least one referral or (ii) the external information associated with the at least one referral;
      automatically perform an insurance pre-authorization process and schedule an appointment request by coordinating with a specialist office and a patient based on the requirements of the at least one referral;
      generate a patient follow-up letter for the appointment request and mail the patient follow-up letter to the patient;
      communicate with the referral provider on additional information required on the at least one referral and update a specialist office about patient appointment;
      follow-up with the specialist office on the referral status after the patient appointment; and
      validate the report and complete or close the at least one referral.

2. The system of claim 1, wherein the processor is configured to automatically enable the specialist to perform at least one action on the at least one referral based on the priorities of the specialist, wherein the referral information associated with the at least one referral is provided to the specialist to perform at least one action on the at least one referral, wherein the at least one action comprises
   (i) generate or customize at least one of workflow, a dynamic widget, self-guiding and surveys or a referral report that corresponds to the at least one referral and the referral provider;
   (ii) manage facility, plugin, the at least one template; and
   (iii) import or export at least one of the referral information or the external information between the at least one external database.

3. The system of claim 1, wherein the processor is further configured to enable a communication between at least one of: the referral provider, at least one user or at least one specialist in the referral eco-environment, wherein the system integrates with a communication tool to enable the communication.

4. The system of claim 1, wherein the processor is further configured to generate at least one automated customizable workflow based on a requirement associated with the at least one referral, wherein the at least one automated customizable workflow comprises triggering an automated notification, creating tasks, creating multiple status to determine a lifecycle of the at least one referral.

5. The system of claim 1, wherein the processor is further configured to transform the referral information and external information into a predetermined format to store in the database, wherein the referral information and the external information are imported and exported from various databases, wherein the external information comprises at least one of patient information or insurance information.

6. The system of claim 1, wherein the processor is further configured to enable the user to generate dynamic widgets based on the requirement of the user and the referral, wherein the dynamic widgets are generated based on user types, wherein the user type comprises operational data for (i) referral coordinators, (ii) staffs and (iii) overall practice performance data for at least one of management users or administrators.

7. The system of claim 1, wherein the processor is further configured to generate the referral report that corresponds to the at least one referral at a periodic instance using selected data from the referral information and the external information, wherein the referral report comprises an organizational report and a referral provider report, wherein the selected data comprises at least one of patient demographics, a clinical information or a clinical chart, a reason for referral, a specialist name, the referral provider and their contact details and associated documents.

8. The system of claim 5, wherein the processor is further configured to perform at least one of:
enable the user to set at least one configuration for the system, wherein the at least one configuration comprises at least one of date, time, title, color, logo, fonts or timeout;
maintain facilities provided by an organization, wherein the facilities comprises at least one of a guest room, a cloak room, or a vehicle parking;
manage user identities and access details to customize the referral report based on the requirement of the at least one referral, wherein the user identities comprise at least one of password resets, creating and provisioning, blocking, deleting or credentials of a plurality of patients;
manage core data of the organization for automatically performing a plurality of actions based on the at least one referral, wherein the core data comprises at least one of a specialty, an insurance, Medications, Vitals, Allergies or Language of the organization;
automatically generate and run a workflow for each referral based on the requirement of the at least one referral, wherein the processor is configured to monitor a process consistency, eliminating errors and problems due to lost or mishandled requests;
manage an update and new features of the system, wherein the processor is configured to enable installation, update and uninstall of applications with the system;
improve a quality of the service by generating self-guiding and interactive online surveys which are needed for the organization;
generate, maintain and control the at least one template of the system that is used for at least one of referral management or data management;
generate customized lightweight components and modules based on the requirements to eliminate a need of scripts writing and enable the user to seamlessly add data;
define own roles and assigns on a need to know basis, wherein a user access may restricted on a basis of internal or external departments/facilities; or
import and export information of the referral associated with the referral provider, the plurality of patients and one or more specialists.

9. A method for managing at least one referral and automatically generating and prioritizing a referral queue to process follow-up and close the at least one referral in a health care-environment, the method comprising:
receiving the at least one referral from at least one of (i) a referral provider via a referral provider device or (ii) a user via a user device;
validating the at least one referral to identify a type of the referral and communicating to the referral provider;
receiving at least one specialist determined by the referral provider based on the type of the at least one referral;
communicating the at least one referral to the at least one specialist;
performing a prioritization based on requirements of the at least one referral by analysing the referral information associated with the at least one referral to automatically generate the referral queue, wherein the referral information comprises at least one of patient demographics, clinical information, clinical charts, a reason for a referral, details of a specialist or referral provider details, wherein the referral information associated with the at least one referral is retrieved from the database based on the referral queue, and external information associated with the at least one referral is automatically searched and retrieved from at least one external database when the at least one referral requires the external information associated with the at least one referral;
determining the at least one action based on the requirements of the at least one referral by generating a report that populates a template using at least one of (i) the referral information associated with the at least one referral or (ii) the external information associated with the at least one referral;
automatically performing an insurance pre-authorization process and scheduling an appointment request by coordinating with a specialist office and a patient based on the requirements of the at least one referral;
generating a patient follow-up letter for the appointment request and mail the patient follow-up letter to the patient;
communicating with the referral provider on additional information required on the at least one referral and updating a specialist office about patient appointment;
following-up with the specialist office on the referral status after the patient appointment; and
validating the report and completing or closing the at least one referral.

10. The method as claimed in claim 9, wherein the method comprises automatically enabling the specialist to perform at least one action on the at least one referral based on the priorities of the specialist, wherein the referral information associated with the at least one referral is provided to the specialist to perform actions on the at least one referral, wherein the at least one action comprises
(i) generating or customizing at least one of workflow, a dynamic widget, self-guiding and surveys or a referral report that corresponds to the at least one referral and the referral provider;
(ii) managing facility, plugin, the at least one template; and
(iii) importing or exporting at least one of the referral information or the external information between the at least one external database.

11. The method as claimed in claim 9, wherein the method comprises enabling a communication between at least one of: the referral provider, at least one user or at least one specialist in the referral eco-environment, wherein the system integrates with a communication tool to enable the communication.

12. The method as claimed in claim 9, wherein the method comprises generating at least one automated customizable workflow based on a requirement associated with the at least one referral, wherein the at least one automated customizable workflow comprises triggering an automated notification, creating tasks, creating multiple status to determine a lifecycle of the at least one referral.

13. The method as claimed in claim 9, wherein the method comprises transforming the referral information and the external information into a predetermined format to store in the database, wherein the referral information and the external information are imported and exported from various databases, wherein the external information comprises at least one of patient information or insurance information.

14. The method as claimed in claim 9, wherein the method comprises enabling the user to generate dynamic widgets based on the requirement of the user and the referral, wherein the dynamic widgets are generated based on user types, wherein the user type comprises operational data for (i) referral coordinators, (ii) staffs and (iii) overall practice performance data for at least one of management users or administrators.

15. The method as claimed in claim 9, wherein the method comprises generating the referral report that corresponds to the at least one referral at a periodic instance using selected data from the referral information and the external information, wherein the referral report comprises an organizational report and a referral provider report, wherein the selected data comprises at least one of patient demographics, a clinical information or a clinical chart, a reason for referral, a specialist name, the referral provider and their contact details and associated documents.

16. The method as claimed in claim 9, wherein the method comprises at least one of
enabling the user to set at least one configuration for the system, wherein the at least one configuration comprises at least one of date, time, title, color, logo, fonts or timeout;

maintaining facilities provided by an organization, wherein the facilities comprises at least one of a guest room, a cloak room, or a vehicle parking;

managing user identities and access details to customize the report based on the requirement of the at least one referral, wherein the user identities comprises at least one of password resets, creating and provisioning, blocking, deleting or credentials of a plurality of patients;

managing core data of the organization for automatically performing a plurality of actions based on the at least one referral, wherein the core data comprises at least one of a specialty, an insurance, Medications, Vitals, Allergies or Language of the organization;

automatically generating and run a workflow for each referral based on the requirement of the at least one referral, wherein the processor is configured to monitor a process consistency, eliminating errors and problems due to lost or mishandled requests;

managing an update and new features of the system, wherein the processor is configured to enable installation, update and uninstall of applications with the system;

improving a quality of the service by generating self-guiding and interactive online surveys which are needed for the organization;

generating, maintain and control the at least one template of the system that is used for at least one of referral management or data management;

generating customized lightweight components and modules based on the requirements to eliminate a need of scripts writing and enable the user to seamlessly add data;

defining own roles and assigns on a need to know basis, wherein an user access may restricted on a basis of internal or external departments/facilities; or importing and exporting information of the referral associated with the referral provider, the plurality of patients and one or more specialists.

* * * * *